United States Patent [19]

Wygant

[11] Patent Number: 4,490,528
[45] Date of Patent: Dec. 25, 1984

[54] PRODUCTION OF CHLORO-S-TRIAZINE TRIONES

[75] Inventor: James C. Wygant, Creve Coeur, Mo.

[73] Assignee: Monsanto Company, St. Louis, Mo.

[21] Appl. No.: 518,861

[22] Filed: Aug. 1, 1983

[51] Int. Cl.³ .................. C07D 251/28; C07D 251/36
[52] U.S. Cl. .................................................. 544/190
[58] Field of Search ......................................... 544/190

[56] References Cited

U.S. PATENT DOCUMENTS 3,453,274  7/1969  Murinn et al. ...................... 544/190
3,757,018  9/1973  Mesiah ............................... 544/190
3,898,222  8/1975  Hill .................................... 544/190

Primary Examiner—John M. Ford
Attorney, Agent, or Firm—J. H. Beusen; J. C. Logomasini; A. H. Cole

[57] ABSTRACT

A process for producing chloro-s-triazine trione with improved crystal properties comprising reacting cyanuric acid, alkali metal hydroxide, and chlorine in water, and crystallizing the resulting chloro-s-triazine trione in the presence of an alpha olefin sulfonate with from 4 to 20 carbon atoms.

8 Claims, No Drawings

PRODUCTION OF CHLORO-S-TRIAZINE TRIONES

FIELD OF THIS INVENTION

The present invention relates to an improved process for manufacturing chloro-s-triazine triones which are sometimes referred to as chlorocyanuric acids or chloroisocyanuric acids. More specifically, this invention pertains to a method for preparing chloro-s-triazine triones, particularly trichloro-s-triazine trione, having enhanced crystal properties.

BACKGROUND

The preparation of chloro-s-triazine triones such as trichloro-s-triazine trione or dichloro-s-triazine trione is well known in the prior art.

One method for producing chloro-s-triazine trione is described in U.S. Pat. No. 2,969,360 issued Jan. 24, 1961. In this process, cyanuric acid (also known as s-triazine trione) is fed along with aqueous alkali metal hydroxide (in molar ratio to the cyanuric acid equal to the number of chlorine atoms per molecule of the desired product) and chlorine to an aqueous reaction zone which is maintained at a pH near 3.5. The feed ingredients are added in essentially stoichiometric proportions. Crude chloro-s-triazine trione precipitates from the solution, to form a slurry. The product slurry is filtered to separate the crystalline product from the mother liquor, and the crystalline product is dried.

The crystal properties of the chloro-s-triazine trione have a marked effect on the trouble-free operation of the process. It is preferred that the crystals of chloro-s-triazine trione be as large as possible. The crystal habit can also effect the ease and efficiency of filtration and drying of the product. The crystal habit of the product can also affect its chlorine stability. Crystal modifiers can be used to enhance the crystal properties of the product to increase its crystal size and change its crystal habit to improve the properties of the product.

Various substances have been proposed in the patent literature to act as crystal modifiers in the production of chloro-s-triazine triones. U.S. Pat. No. 3,120,522 issued Feb. 4, 1964 uses a chlorinated hydrocarbon with from 1 to 6 carbon atoms and not more than one hydrogen atom per molecule. U.S. Pat. No. 3,453,274 issued July 1, 1969 uses alkali metal sulfates or alkali metal alkylarylsulfonates. U.S. Pat. No. 3,941,784 issued Mar. 2, 1976 uses a small amount of polyoxyethylene, polyoxypropylene, or copolymers of polyoxyethylene and polyoxypropylene. U.S. Pat. No. 4,087,608 issued May 2, 1978 uses alkylated diphenyloxide disulfonic acid or alkali metal salts thereof.

The object of this invention is to provide a chloro-s-triazine trione product having improved properties, as a result of enhanced crystal properties.

SUMMARY OF THE INVENTION

A process for producing crystalline chloro-s-triazine trione, such as trichloro-s-triazine trione or dichloro-s-triazine trione by reacting cyanuric acid with an alkali metal hydroxide in water to form an aqueous reaction mixture; further reacting the aqueous reaction mixture with chlorine to form the chloro-s-triazine trione; forming crystals of the chloro-s-triazine trione in the presence of an effective amount, preferably from about 20 to about 500 parts per million by weight of the aqueous reaction mixture and most preferably from about 125 to about 200 parts per million, of an alpha olefin sulfonate crystal modifier which contains from 4 to 20 carbon atoms, preferably from 6 to 16 carbon atoms and most preferably averaging about 10 carbon atoms; and separating the crystalline chloro-s-triazine trione from the remainder of the aqueous reaction mixture. The alpha olefin sulfonate may be either the acid or a salt. Salts are preferably alkali metal salts with sodium and potassium being most preferred.

DESCRIPTION OF THE PREFERRED EMBODIMENT

A preferred method of manufacturing trichloro-s-triazine trione to which this invention is applicable is to mix a slurry of substantially pure cyanuric acid with alkali metal hydroxide (e.g. sodium or potassium hydroxide, preferably sodium) to prepare an aqueous solution. To prepare trichloro-s-triazine trione, the molar ratio of hydroxide to cyanuric acid should be about 3:1, and to prepare dichloro-s-triazine trione, the molar ratio of hydroxide to cyanuric acid should be about 2:1. An intermediate molar ratio of hydroxide to cyanuric acid will produce a mixture of dichloro-s-triazine trione and trichloro-s-triazine trione. The solution is then fed continuously to a reactor to which chlorine and the crystal modifier are also fed continuously. Temperature of the reactor contents is maintained at about 15°–25° C. with pH maintained in the range from about 1.0 to about 4.5, preferably between 3.0 and 4.5. For trichloro-s-triazine trione, the most preferred pH range is between 3.5 and 4.0. The crystal modifier feed rate is adjusted to maintain the concentration of the crystal modifier at an effective level. It is preferred that the crystal modifier be present from about 20 to about 500 ppm by weight and more preferably from about 125 to about 200 ppm by weight, based upon the reactor contents.

The crystal modifier for use herein is an alpha olefin sulfonate in which the olefin contains from 4 to 20 carbon atoms. The preferred crystal modifier is an alpha olefin sulfonate in which the olefin contains from 6 to 16 carbon atoms, and most preferably 10 carbon atoms. It is also possible to use a mixture of alpha olefin sulfonates in which chain length of the olefin substituent varies, provided the average chain length is from about 4 to about 20 carbon atoms and more preferably from about 6 to about 16 carbon atoms and most preferably about 10 carbon atoms.

The product chloro-s-triazine trione precipitates out of the reaction mixture, is withdrawn from the reactor as a slurry, is then filtered, dried, and packaged. When produced using the alpha olefin sulfonates described above, the product obtained dries more readily and completely, produces a larger crystal size, and produces a product with enhanced chlorine stability. The exact mechanism by which these results are produced is not fully understood.

The following Examples illustrate this invention but are not intended to any way limit its scope. All parts and percentages herein are by weight unless otherwise specified.

EXAMPLES 1–30

In all Examples 1–30, the following continuous procedure was used to produce the trichloro-s-triazine trione.

The apparatus used was a reactor adapted to agitate the reaction mixture and cool it to about 20°–25° C. The reactor was equipped with a bubbler to bubble chlorine into the reaction mixture and a scrubber to remove gaseous chlorine from the vapor space in the reactor.

Feed solution was prepared by mixing sodium hydroxide and cyanuric acid in a mole ratio of about 3 in water. Chlorine was bubbled into the reaction mixture at a rate to maintain the pH at or below 3.75. The cyanuric acid feed solution was added through the scrubber to remove gaseous chlorine from the effluent gas and then was added to the reaction mixture. The indicated crystal modifier was added at a rate to maintain the specified concentration. The trichloro-s-triazine trione crystallized out of the reaction mixture, and was withdrawn periodically as a slurry to maintain the desired volume within the reactor. The slurry was filtered and air dried at ambient conditions for about 16 hours.

In Examples 1-30, various alpha olefin sulfonates were used as the crystal modifier. Three different $C_{10}$ alpha olefin sulfonates were used in Examples 1-25. Three different $C_{14-16}$ alpha olefin sulfonates were used in Examples 26-28. And, two different $C_{6-10}$ alpha olefin sulfonates were in Examples 29 and 30. Various concentration ranges were used, expressed as parts per million (ppm) of the contents of the reactor. The following tests were done to determine the effectiveness of the crystal modifier.

The first test was to determine the ease of drying of the product. A sample of the product was placed in a 105° C. oven and dried for 2 hours, to drive off all remaining moisture. The amount of weight loss during this oven drying for Examples 1-30 is reported as 105° C. LOD. A lower number indicates a smaller amount of water remaining in the product after air drying. This 105° C. LOD should be below about 0.15, preferably below about 0.10 and most preferably about 0.05. The more completely the product air dries, the more easily it can be dried in continuous plant drying equipment and the more trouble-free will be the drying operation. Additionally, a product that air dries more completely will be less likely to re-absorb moisture on exposure to humid conditions.

The second test indicated the crystal size of the product being produced. The product was screened with a 140 mesh screen, and the percentage of the product retained by this 140 mesh screen is reported as % retained 140 screen. A larger number indicates a smaller proportion of very fine crystals, and indicates an increase in crystal size of the product. At least about 50% of the product should be retained on a 140 mesh screen, and preferably at least about 60%.

The chlorine stability of the product of each Example was evaluated by placing 100 grams of the dried product in an 8 ounce sealed bottle, which was stored in a 50° C. oven for 24 hours. After cooling to room temperature, the percent of chlorine gas in the vapor space inside the bottle was determined by dissolving a sample of the vapor in water followed by amperometric titration with phenylarseneoxide. These results are reported % $Cl_2$ gas. This value should be below 10.0, preferably below about 4.0, more preferably below about 2.0 and most preferably below about 1.0.

The results of Examples 1-30 are shown in Table I.

TABLE I

| EX NO. | CRYSTAL MODIFIER | PPM | 105° C. LOD | % RETAINED 140 SCREEN | % $Cl_2$ GAS |
|---|---|---|---|---|---|
| 1 | $C_{10}$AOS #1[a] | 170 | .06 | 69 | 1.3 |
| 2 | " | 167 | .05 | 76 | 0.6 |

TABLE I-continued

| EX NO. | CRYSTAL MODIFIER | PPM | 105° C. LOD | % RETAINED 140 SCREEN | % $Cl_2$ GAS |
|---|---|---|---|---|---|
| 3 | " | 160 | .05 | 71 | 0.7 |
| 4 | " | 132 | .05 | 59 | 1.0 |
| 5 | " | 98 | .07 | 59 | 1.6 |
| 6 | " | 70 | .07 | 59 | 1.5 |
| 7 | $C_{10}$AOS #2[b] | 229 | .07 | 67 | 2.2 |
| 8 | " | 203 | .05 | 67 | 1.1 |
| 9 | " | 182 | .06 | 52 | 1.0 |
| 10 | " | 172 | .06 | 73 | 0.9 |
| 11 | " | 164 | .08 | 61 | 1.8 |
| 12 | " | 148 | .09 | 64 | 2.3 |
| 13 | " | 136 | .14 | 48 | 9.7 |
| 14 | " | 133 | .10 | 60 | 3.2 |
| 15 | " | 129 | .11 | 48 | 5.9 |
| 16 | " | 102 | .07 | 54 | 8.4 |
| 17 | $C_{10}$AOS #3[c] | 240 | .10 | 68 | 2.3 |
| 18 | " | 232 | .06 | 75 | 2.3 |
| 19 | " | 180 | .07 | 63 | 2.2 |
| 20 | " | 179 | .08 | 68 | 2.1 |
| 21 | " | 178 | .06 | 67 | 2.2 |
| 22 | " | 134 | .13 | 66 | 3.6 |
| 23 | " | 129 | .11 | 68 | 7.0 |
| 24 | " | 110 | .16 | 54 | 25.2 |
| 25 | " | 106 | .18 | 55 | 25.9 |
| 26 | Bio Terg 40[d] | 176 | .15 | 11 | 10.4 |
| 27 | Siponate A246-L[e] | 174 | .11 | 54 | 5.7 |
| 28 | Witconate AOS[f] | 172 | .08 | 51 | 2.5 |
| 29 | Witconate 3202[g] | 209 | .07 | 58 | 2.4 |
| 30 | Witconate 3203[h] | 150 | .11 | 54 | 13.6 |

[a]Obtained from Gulf Chemical Co.
[b]Obtained from Witco Chemical Co.
[c]Obtained from Witco Chemical Co.
[d]Product of Stepan Chemical Co., a $C_{14-16}$ alpha olefin sulfonate
[e]Product of Alcolac Chemical Corp., a $C_{14-16}$ alpha olefin sulfonate
[f]Product of Witco Chemical Co., a $C_{14-16}$ alpha olefin sulfonate
[g]Product of Witco Chemical Co., a $C_{6-10}$ alpha olefin sulfonate
[h]Product of Witco Chemical Co., A $C_{6-10}$ alpha olefin sulfonate As a comparison, Examples 31-41 were run using a procedure similar to that used for Examples 1-30, except that Example 31 used no crystal modifier and Examples 32-41 used crystal modifiers outside the scope of this invention. The results of Examples 31-41 are shown in Table II.

TABLE II

| EX NO | CRYSTAL MODIFIER | PPM | 105° C. LOD | % RETAINED 140 SCREEN | % $Cl_2$ GAS |
|---|---|---|---|---|---|
| 31 | None | — | .15 | 11 | 11.5 |
| 32 | Dowfax 2A1[a] | 172 | .08 | 55 | 3.0 |
| 33 | Dowfax 2A1[a] | 129 | .09 | 25 | 5.4 |
| 34 | Dowfax 3B2[b] | 228 | .12 | 44 | 16.9 |
| 35 | Dowfax 3B2[b] | 164 | .11 | 33 | 8.0 |
| 36 | Petro BA[c] | 194 | .10 | 59 | 4.4 |
| 37 | Petro BP[c] | 202 | .21 | 69 | 15.2 |
| 38 | $C_6$ Alkane Sulfonate[d] | 172 | .16 | 50 | 8.9 |
| 39 | $C_{10}$ Alkane Sulfonate[d] | 174 | .09 | 67 | 5.8 |
| 40 | $C_{12}$ Alkane Sulfonate[d] | 188 | .11 | 59 | 5.2 |
| 41 | Sulfonated Castor Oil[e] | 172 | .16 | 50 | 8.9 |

[a]Product of Dow Chemical Co., a dodecyl diphenyl oxide disulfonate
[b]Product of Dow Chemical Co., a decyl diphenyl oxide disulfonate
[c]Product of Petrochemicals Co., Inc., both alkyl napthalene sulfonates
[d]Obtained from Witco Chemical Co.
[e]Obtained from Proctor Chemical Co.

A comparison of Examples on Table II with Examples on Table I with similar concentrations of crystal modifier shows that alpha olefin sulfonates are superior to alkylated dodecyl diphenyl oxide disulfonates, alkyl napthalene sulfonates, and even superior to the very structurally similar alkane sulfonates.

The threshold value at which the alpha olefin sulfonate becomes effective as a crystal modifier varies based upon the actual alpha olefin sulfonate being used. The cause of these observed differences is not understood, but it is believed to result from differences in sulfonation procedure used and in the olefin from which the alpha olefin sulfonate is prepared. The exact threshold of effectiveness cannot be predicted, but can very easily be determined for the specific alpha olefin sulfonate being considered. The alpha olefin sulfonate is considered to be effective when it produces one or more of the following results:

(1) a lower LOD value than product produced using no crystal modifier;

(2) a larger crystal size than product produced using no crystal modifier; and (3) a lower % $Cl_2$ gas than product produced using no crystal modifier.

However, best results are usually obtained when the alpha olefin sulfonate is present from about 20 ppm to about 500 ppm by weight based upon the reactor contents, and preferably from about 125 ppm to about 200 ppm.

EXAMPLE 41

Trichloro-s-triazine trione was produced on a continuous basis, using a process similar to that used in Examples 1–40, except that the product slurry was removed from the reactor continuously, was then filtered, was reslurried with water to wash the product, and was then centrifuged. Drying was then done in a flash dryer for a short period of time at 100°–120° C. This process was run for about 4–5 days using $C_{10}AOS$ #3 as the crystal modifier at concentrations between 230 ppm and 180 ppm. Variations within this range for this $C_{10}AOS$ did not substantially affect product quality. During this period 4 product samples were taken at random. Crystal size was evaluated as the percent of the product retained on a 100 mesh screen and on a 200 mesh screen, instead of the 140 mesh screen used in Examples 1–40. Also, the loss on drying test was done at 85° C. instead of 105° C. Comparative extended runs were done both before and after these $C_{10}AOS$ runs, except that Dowfax 2A1 was used as the crystal modifier. During these Comparative runs, 13 product samples were taken and evaluated in a manner similar to the $C_{10}AOS$ runs. The average results for each of these two crystal modifiers is shown on Table III.

TABLE III

| CRYSTAL MODIFIER | PPM | 85° C. LOD | % RETAINED 100 SCREEN | % RETAINED 200 SCREEN | % $CL_2$ GAS |
|---|---|---|---|---|---|
| $C_{10}AOS$ #3 | 180–203 | .06 | 44 | 82 | 2.7 |
| Dowfax 2A1 | 175 | .07 | 32 | 79 | 2.3 |

During the extended tests of Example 41, the alpha olefin sulfonate exhibited no foaming in any of the vessels used in the process. This is compared with the Dowfax 2A1 which exhibited some minor foaming. Previously, a similar extended test using an alkyl benzene sulfonate had to be terminated due to excessive amounts of foaming.

While the crystal modifiers of the present invention have been mainly described in connection with the manufacture of trichloro-s-triazine trione, the utility is not limited thereto. Superior results will also be achieved in the manufacture of dichloro-s-triazine trione.

I claim:

1. A process of producing crystalline chloro-s-triazine trione comprising: reacting cyanuric acid with an alkali metal hydroxide in water to form an aqueous reaction mixture; further reacting the aqueous reaction mixture with chlorine to form chloro-s-triazine trione; forming crystals of the chloro-s-triazine trione in the presence of an effective amount an alpha olefin sulfonate crystal modifier which contains from 4 to 20 carbon atoms; and separating the crystalline chloro-s-triazine trione from the remainder of the aqueous reaction mixture.

2. The process of claim 1 wherein the alpha olefin sulfonate crystal modifier is present from about 20 to about 500 parts per million by weight of the aqueous reaction mixture.

3. The process of claim 1 wherein the alpha olefin sulfonate crystal modifier is present from about 125 to about 200 parts per million by weight of the aqueous reaction mixture.

4. The process of claim 1 wherein the alpha olefin sulfonate crystal modifier contains from about 6 to about 16 carbon atoms.

5. The process of claim 1 wherein the alpha olefin sulfonate crystal modifier contains an average of about 10 carbon atoms.

6. The process of claim 1 wherein the alkali metal hydroxide is sodium hydroxide.

7. The process of claim 1 wherein the chloro-s-triazine trione produced is trichloro-s-triazine trione.

8. A process for preparing crystalline trichloro-s-triazine trione, comprising reacting cyanuric acid with sodium hydroxide in water to form an aqueous reaction mixture; further reacting the aqueous reaction mixture with chlorine to form trichloro-s-triazine trione; forming crystals of trichloro-s-triazine trione in the presence of from about 125 to about 200 parts per million by weight of the aqueous reaction mixture of an alpha olefin sulfonate containing an average of about 10 carbon atoms; and separating the crystalline trichloro-s-triazine trione from the remainder of the aqueous reaction mixture.

* * * * *